United States Patent
Simpson et al.

(10) Patent No.: US 11,111,510 B2
(45) Date of Patent: *Sep. 7, 2021

(54) FERMENTATION PROCESS FOR THE PRODUCTION OF LIPIDS

(71) Applicants: LanzaTech New Zealand Limited, Skokie, IL (US); DBT-IOC Centre for Advanced Bio-Energy Research, Faridabad (IN)

(72) Inventors: Sean Dennis Simpson, Skokie, IL (US); Sebastian Michal Bernasek, Skokie, IL (US); Deepak K Tuli, Faridabad (IN)

(73) Assignees: LanzaTech New Zealand Limited, Skokie, IL (US); DBT-IOC Centre for Advanced Bio-Energy Research, Faridabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/723,498

(22) Filed: Dec. 20, 2019

(65) Prior Publication Data

US 2020/0123580 A1    Apr. 23, 2020

Related U.S. Application Data

(63) Continuation of application No. 14/927,950, filed on Oct. 30, 2015, now Pat. No. 10,570,427.

(60) Provisional application No. 62/073,584, filed on Oct. 31, 2014.

(51) Int. Cl.
   *C12P 7/64*     (2006.01)
   *C12P 39/00*    (2006.01)

(52) U.S. Cl.
   CPC ........... *C12P 7/6427* (2013.01); *C12P 7/6463* (2013.01); *C12P 7/6472* (2013.01); *C12P 39/00* (2013.01); *Y02E 50/10* (2013.01)

(58) Field of Classification Search
   None
   See application file for complete search history.

(56) References Cited

U.S. PATENT DOCUMENTS

| | | | | |
|---|---|---|---|---|
| 2001/0046691 A1* | 11/2001 | Bailey | .................... | C12N 1/12 435/134 |
| 2007/0245431 A1* | 10/2007 | Metz | .................... | A61P 1/16 800/281 |
| 2009/0047721 A1* | 2/2009 | Trimbur | .................... | C12N 1/32 435/167 |
| 2010/0105115 A1* | 4/2010 | Simpson | .................... | C12P 7/16 435/135 |

FOREIGN PATENT DOCUMENTS

WO   WO-2008094282 A1 *  8/2008   ............ C12M 23/34

OTHER PUBLICATIONS

Ren, Hong-Yu et al. A new lipid-rich microalga *Scenedesmus* sp. Strain R-16 isolated using Nile red staining: effects of carbon and nitrogen sources and initial pH on the biomass and lipid production. Biotechnology for Biofuels 2013, 6:143 (Year: 2013).*

* cited by examiner

*Primary Examiner* — Nghi V Nguyen
(74) *Attorney, Agent, or Firm* — Frank S. Molinaro

(57) ABSTRACT

The invention provides methods and systems for the production of lipid products from a gaseous substrate using a two stage fermentation process. The method comprises providing a gaseous substrate comprising CO, $CO_2$ or $H_2$ or mixtures thereof, to a first bioreactor containing a culture or one or more microorganisms, and fermenting the substrate to produce acetate. The acetate from the first bioreactor is then provided to a second bioreactor, where it is used as a substrate for fermentation to lipids by one or more microalgae.

18 Claims, 2 Drawing Sheets

FERMENTATION PROCESS FOR THE PRODUCTION OF LIPIDS

CROSS REFERENCE TO RELATED APPLICATIONS

This application is a continuation of U.S. patent application Ser. No. 14/927,950 filed Oct. 30, 2015, which claims the benefit of U.S. Provisional Patent Application 62/073,584 filed Oct. 31, 2014, the entirety of which is incorporated herein by reference.

FIELD OF THE INVENTION

This invention relates to a method for the production of lipids from gaseous feedstock. The method comprises a two stage system for the production of one or more lipid products from a gaseous feedstock.

BACKGROUND OF THE INVENTION

The global energy crisis has caused increased interest in alternative approaches to production of fuels. Biofuels for transportation are attractive replacements for gasoline and are rapidly penetrating fuel markets as low concentration blends. Biomass derived biofuel production has emerged as a major approach in increasing alternative energy production and reducing greenhouse gas emissions. The production of biofuels from biomass enables energy independence has been shown to enhance development of rural areas and enhance sustainable economic development.

First generation liquid biofuels utilise carbohydrate feedstocks such as starch, cane sugar, corn, rapeseed, soybean, palm and vegetable oils. The first generation feedstocks present a number of significant challenges. The cost of these carbohydrate feed stocks is influenced by their value as human food or animal feed, while the cultivation of starch or sucrose-producing crops for ethanol production is not economically sustainable in all geographies. The sustained use of these feedstocks as a source for biofuels would inevitably place great strain on arable land and water resources. Therefore, it is of interest to develop technologies to convert lower cost and/or more abundant carbon resources into fuels.

Second generation biofuels are those produced from cellulose and algae. Algae were selected to produce lipids due to their rapid growth rates and the ability of algae to consume carbon dioxide and produce oxygen.

One area that has seen increased activity is the microbial synthesis of lipids which comprise the raw materials required for bio fuel production. Numerous studies have demonstrated an ability to accumulate lipids through the use of oleaginous yeasts on different substrates such as industrial glycerol, acetic acid, sewage sludge, whey permeate, sugar cane molasses and rice straw hydrolysate. Again these second generation biofuel technologies have encountered problems due to high production costs, and costs associated with the transport and storage of the feedstock.

It has long been recognised that catalytic processes may be used to convert gases consisting of CO, $CO_2$, or hydrogen ($H_2$) into a variety of fuels and chemicals. However, microorganisms may also be used to convert these gases into fuels and chemicals. These biological processes, although generally slower than thermochemical processes, have several advantages over catalytic processes, including higher specificity, higher yields, lower energy costs and greater resistance to poisoning.

The production of acetic acid, acetate and other products such as ethanol by the anaerobic fermentation of carbon monoxide, and/or hydrogen and carbon dioxide has been demonstrated. See, e.g., Balch et al, (1977) International Journal of Systemic Bacteriology, 27:355-361; Vega et al, (1989) Biotech. Bioeng., 34:785-793; Klasson et al (1990) Appl. Biochem. Biotech., 24/25: 1; among others.

Acetogenic bacteria, such as those from the genus *Acetobacterium, Moorella, Clostridium, Ruminococcus, Acetobacterium, Eubacterium, Butyribacterium, Oxobacter, Methanosarcina, Methanosarcina*, and *Desulfotomaculum* have been demonstrated to utilize substrates comprising $H_2$, $CO_2$ and/or CO and convert these gaseous substrates into acetic acid, ethanol and other fermentation products by the Wood-Ljungdahl pathway with acetyl co-A synthase being the key enzyme. For example, various strains of *Clostridium ljungdahlii* that produce acetate and ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce acetate and ethanol from gases (Aribini et al, Archives of Microbiology 161, pp 345-351 (1994)).

*Acetobacterium woodii*, a strictly anaerobic, non-spore forming microorganism that grows well at temperatures of about 30° C., has been shown to produce acetate from $H_2$ and $CO_2$. Balch et al. first disclosed the bacterium *A. woodii* which grows by the anaerobic oxidation of hydrogen and reduction of carbon dioxide. Buschorn et al showed the production and utilisation of ethanol by *A. woodii* on glucose. Fermentation of *A. woodii* was performed at glucose (fructose) concentrations of up to 20 mM. Buschorn et al found that when the glucose concentration was increased to 40 mM, almost half of the substrate remained when *A woodii* entered the stationary growth phase, and ethanol appeared as an additional fermentation product. Balch et al found that the only major product detected by the fermentation of $H_2$ and $CO_2$ by *A. woodii* was acetate according to the following stoichiometry; $4H_2 + 2CO_2 \rightarrow CH_3COOH + H_2O$.

Acetate can be an undesirable fermentation product, as it is challenging product to recover from an aqueous fermentation broth and has limited commercial use.

It is an object of the present invention to provide a process and fermentation system that goes at least some way towards overcoming the above disadvantages, or at least to provide the public with a useful choice.

SUMMARY OF THE INVENTION

In a first aspect there is provided a method for producing at least one lipid product from a gaseous substrate, the method comprising;
i. receiving the gaseous substrate in a first bioreactor containing a culture of at least one microorganism, and fermenting the gaseous substrate to produce at least one acid and or alcohol; and
ii. passing at least a portion of the at least one acid and or alcohol to a second bioreactor containing a culture of at least one microalgae, and fermenting the acids to produce at least one lipid product.

In one embodiment, the gaseous substrate comprises CO, $CO_2$ or $H_2$, or mixtures thereof. In certain embodiments the gaseous substrate is derived from an industrial source. In certain embodiments at least one gas from at least one industrial source are blended to provide a gaseous substrate with a desired composition.

In one embodiment the one or more acids is selected from the group consisting of acetate, butyrate, succinate, lactate or propionate.

In one embodiment the one or more alcohols is selected from the group comprising ethanol, butanol, methanol, or propanol.

In various embodiments all of the acid and/or alcohol produced in the first stage is converted to lipids in the second stage. In various embodiments, at least a portion of the acid(s) and or alcohol(s) produced in the first stage is recovered.

In a second aspect there is provided a method for producing at least one lipid product from a gaseous substrate comprising CO, $CO_2$ or $H_2$, or mixtures thereof, the method comprising;
  i. receiving the gaseous substrate in a primary bioreactor containing a culture of at least one microorganism, and fermenting the gaseous substrate to produce at least one acid; and
  ii. passing at least a portion of the at least one acid to a secondary bioreactor containing a culture of at least one microalgae, and fermenting the at least one acid to produce at least one lipid products.

In one embodiment the at least one acid is acetate and the at least one microorganism is selected from the group consisting of *Acetobacterium, Moorella, Clostridium, Pyrococcus, Eubacterium, Desulfobacterium, Carboxydothermus Acetogenium, Acetoanaerobium, Butyribacterium, Peptostreptococcus Ruminococcus Oxobacter*, and *Methanosarcina*.

Those skilled in the art will appreciate the fermentation conditions, including pH ranges, necessary for the successful fermentation of gaseous substrates comprising CO, $CO_2$ or $H_2$, or mixtures thereof. The inventors acknowledge that any particular acetogenic microorganism that may be used in accordance with the invention will have an optimum pH range, which is typically between pH4 and pH 8. In one embodiment of the invention, the pH of the fermentation in the primary bioreactor is maintained between around pH 4.5 to around pH 6. In a preferred embodiment the pH is maintained at pH 5.5.

In one embodiment the lipids produced in the second reactor are used to produce at least one tertiary product. In one embodiment the one or more tertiary products are selected from the group comprising biodiesel, hydrogenation-derived renewable diesel (HDRD), fatty acid methyl esters (FAME) and fatty acid ethyl esters (FAEE).

In a third aspect there is provided a method for producing at least one product by anaerobic microbial fermentation, the method comprising;
  i. receiving a substrate comprising CO, $CO_2$, or $H_2$, or mixtures thereof, into a first primary bioreactor containing a culture of at least one microorganism selected from the group consisting of *Acetobacterium, Moorella, Clostridium, Ruminococcus, Eubacterium, Butyribacterium, Oxobacter, Methanosarcina, Methanosarcina*, and *Desulfotomaculum*, and anaerobically fermenting the substrate to produce a fermentation broth comprising acetate;
  ii. feeding the fermentation broth into a secondary bioreactor containing a culture of at least one microalgae; and
  iii. fermenting acetate to produce at least one lipids product.

In one embodiment at least a portion of the fermentation broth is passed from the primary bioreactor to the secondary bioreactor as a broth bleed.

In one embodiment products produced in the primary bioreactor are removed as a permeate bleed.

In one embodiment the broth bleed and permeate bleed are combined prior to being fed to the secondary bioreactor.

In one embodiment the combined fermentation broth is processed to remove at least a portion of the acetate prior to the stream being fed to the secondary bioreactor.

In a fourth aspect there is provided a method for controlling pH in a fermentation process, the method comprising:
  i. receiving a gaseous substrate in a first bioreactor containing a culture of at least one microorganism in a liquid nutrient medium, and fermenting the gaseous substrate to produce a broth comprising at least one acid and/or alcohol;
  ii. passing at least a portion of the broth comprising at least one acid and/or alcohol to a second bioreactor containing a culture of at least one microalgae in a liquid nutrient medium, and fermenting the at least one acid to produce at least one lipid product; and
  iii. recycling at least a portion of the broth back to the first bioreactor, wherein the acid concentration in the recycled broth is substantially reduced.

It would be understood that the following embodiments can be applied to any one of the aspects described above.

In one embodiment the pH of the combined fermentation stream is adjusted to be between pH6 and pH8 prior to being fed to the secondary bioreactor.

In various embodiments lipid production in the secondary bioreactor may be increased by limiting at least one nutrient in the media. In one embodiment lipid production in the secondary bioreactor is increased by limiting the amount of nitrogen in the media.

In one embodiment of the invention the ratio of acetic acid to nitrogen in the fermentation broth in the secondary bioreactor is at least 10:1. In one embodiment the ratio of acetic acid to nitrogen in the fermentation broth of the secondary bioreactor is 49:1. In one embodiment of the invention, the acid stream exiting the first bioreactor is treated to provide a purified or concentrated acid stream to be passed to the second bioreactor. In one embodiment of the invention the carbon:nitrogen ratio of the fermentation broth in the second bioreactor is monitored, and the input of carbon and nitrogen to the bioreactor is adjusted to ensure a carbon:nitrogen ratio of greater than 49:1.

In one embodiment of the invention the acetate produced in the primary bioreactor has a concentration of at least about 5 g/L or at least about 10 g/L, or at least about 15 g/L, or at least about 20 g/L.

In one embodiment of the invention the production rate of acetate in the primary bioreactor is at least about 10 g/L/day, or at least 15 g/L/day, or 20 g/L/day or at least about 40 g/L/day, or at least about 60 g/L/day.

In one embodiment of the invention the microalgae is selected from the group comprising *Chlorella, Chlamamydomonas, Dunaliella, Euglena, Parvum, Tetraselmis, Porphyridium, Spirulina, Synechoccus, Anabaena, Schizochytrium, Botyrococcus, Fucus, Parachlorella, Pseudochlorella, Brateococcus, Prototheca, Scenedesmus, Thraustochytrium, Japonochytrium, Aplanochytrium, Elina*, and *Labyrinthula* (or *Labyrinthuloides* or *Labyrinthulomyxa*). In a preferred embodiment, the microalgae is a thraustochytrid of the genus *Thraustochytrium*.

In one embodiment of the invention the pH of the culture in the secondary bioreactor is maintained at between around pH 6 to around pH 8. In a preferred embodiment the pH is maintained at pH 7.

In one embodiment of the invention the pH in the secondary bioreactor is substantially the same as the pH in the primary bioreactor. In alternative embodiments, the pH of the stream exiting the primary bioreactor is adjusted to about pH 7 prior to being fed to the secondary bioreactor.

In one embodiment of the invention the lipid concentration in the second bioreactor is at least about at least 10 g/L or at least about 20 g/L, or at least about 40 g/L, or at least about 60 g/L, or at least about 80 g/L, or at least about 100 g/L, or at least about 150 g/L. In one embodiment of the invention, the lipid production rate in the second bioreactor is at least about 5 g/L/day, or at least about 7 g/L/day, or at least about 10 g/L/day, or about 15/g/L/day, or at least about 20 g/L/day, or at least about 30 g/L/day.

In one embodiment of the invention, the method is a continuous two stage process. In one embodiment, the method is a semi continuous two stage process.

In one embodiment all of the acetate produced in the primary bioreactor is transferred to the secondary bioreactor for fermentation to lipids.

In one embodiment, at least a portion of the acetate produced in the primary bioreactor is recovered.

In one embodiment, at least a portion of the stream exiting the secondary bioreactor is recycled to a primary reactor. In one embodiment, the exit stream is processed to remove substantially all of the biomass prior to being passed to the primary reactor. In certain embodiments the exit stream is further treated to remove soluble proteins and other unwanted components. In other embodiments the pH of the exit stream is adjusted prior to being fed into the primary reactor.

In one embodiment, the exit stream is passed through an oxygen scrubber to remove substantially all of the oxygen prior to being passed to the primary reactor.

In one embodiment the lipids produced in the secondary bioreactor are used to produce at least one tertiary product. In one embodiment the at least one tertiary product is selected from the group comprising biodiesel, HDRD, FAME and FAEE.

In one embodiment a series of primary rectors are used to feed at least one secondary reactor. For example three primary reactors to feed one secondary reactor, four primary reactors feeding two secondary reactors, etc.

In one embodiment the gaseous substrate is a waste or off gas from an industrial process. In one embodiment the waste gas is selected from the group comprising tail gas from a hydrogen plant, coke oven gas, associated petroleum gas, natural gas, catalytic reformer gas, naphtha cracker off gas, refinery fuel gas, methanol plant tail gases, ammonia plant tail gases, and lime kiln gases.

The invention may also includes the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE DRAWINGS

The invention will now be described in more detail and with reference to the accompanying figures, in which.

DETAILED DESCRIPTION OF THE INVENTION

Figure 1:
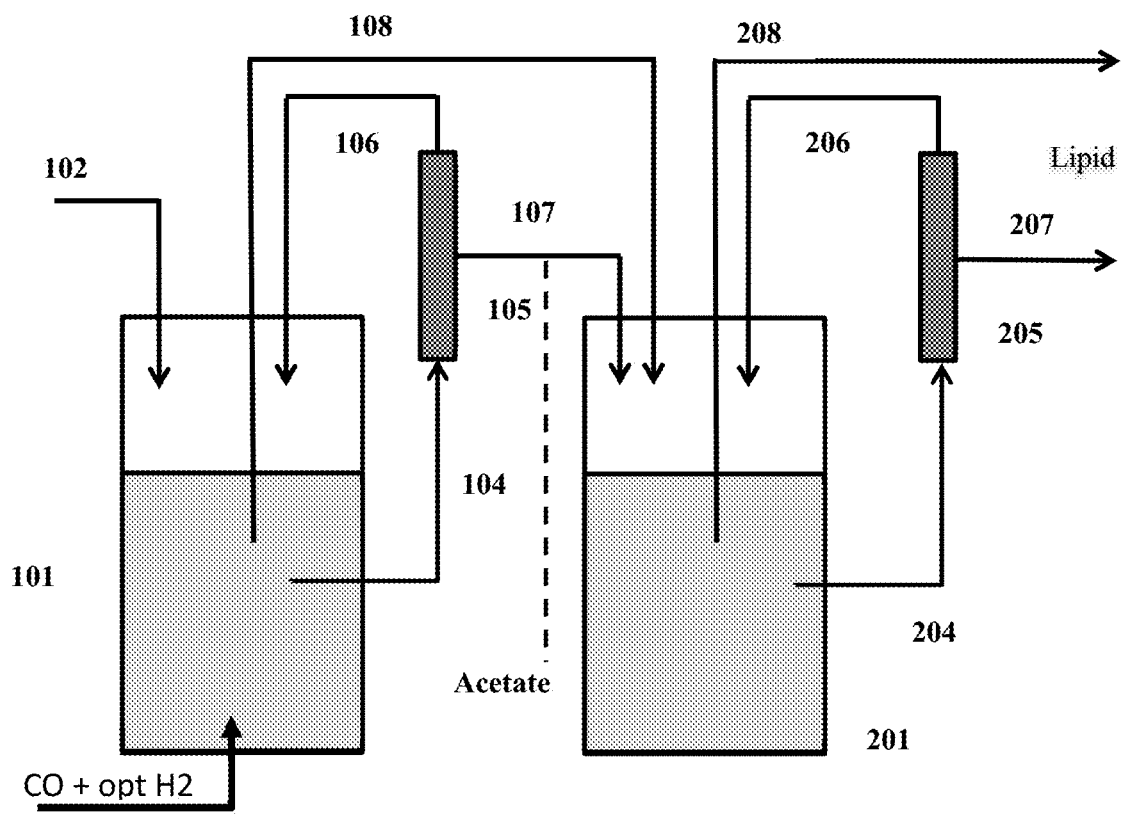
FIG. 1 is a diagram of a two fermenter system for production of lipids from CO and optionally $H_2$, or $CO_2$ and $H_2$, as defined by a second aspect of the present invention.

The present invention generally relates to a process of producing alcohols by fermentation of gaseous substrates containing CO, or $CO_2$ and $H_2$. The methods of the present invention also generally relate to improvements in carbon capture, wherein CO, or $CO_2$ and $H_2$, is converted into useful products, namely lipids.

Definitions

Unless otherwise defined, the following terms as used throughout this specification are defined as follows:

Permeate—substantially soluble constituents of the broth that pass through the separator and are not retained by the separator. The permeate will typically contain soluble fermentation products, by-products and nutrient solution.

Dilution rate—the rate of replacement of the broth in a bioreactor. The dilution rate is measured in the number of bioreactor volumes of broth that are replaced by nutrient medium per day.

Fermentation broth or broth—the mixture of components (including the broth culture and nutrient medium) found in the bioreactor.

Nutrient medium—the solution added to the fermentation broth containing nutrients and other components appropriate for the growth of the microorganism culture.

Gaseous substrate—and like terms should be understood to include any substrate in which carbon monoxide or carbon dioxide is available to one or more strains of bacteria for growth and/or fermentation, for example. Such substrates may optionally comprise $H_2$, which may be present in varying proportions.

Broth bleed—the portion of the fermentation broth removed from a bioreactor that is not passed to a separator.

Broth culture—the microorganism culture present in the fermentation broth.

Broth culture density—the density of microorganism cells in the fermentation broth.

Separator—a module that is adapted to receive fermentation broth from a bioreactor and pass the broth through a filter to yield a retentate and a permeate. The filter may be a membrane, e.g. cross-flow membrane or a hollow fibre membrane.

Acid—as used herein this term includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. The term "acetate" includes both acetate salt alone and a mixture of molecular or free acetic acid and acetate salt, such as the mixture of acetate salt and free acetic acid present in a fermentation broth as may be described herein. The ratio of molecular acetic acid to acetate in the fermentation broth is dependent upon the pH of the system.

Lipid—as used herein include fatty acids, glycolipids, sphingolipids, saccharolipids, polyketides, sterol lipids and prenol lipids. In a preferred embodiment, the lipid is a polyunsaturated fatty acid, such as an omega-3 fatty acid (also called ω-3 fatty acid or n-3 fatty acid). The omega-3 fatty acid may be one or more of alpha-linolenic acid (ALA), eicosapentaenoic acid (EPA), and docosahexaenoic acid (DHA).

Bioreactor or fermenter—includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Moving Bed Biofilm Reactor (MBBR), Bubble Column, Gas Lift Fermenter, Membrane Reactor such as Hollow Fibre Membrane Bioreactor (HFMBR), Static Mixer, or other vessel or other device suitable for gas-liquid contact.

Primary bioreactor—as used herein this term is intended to encompass one or more reactors that may be connected in series or parallel with a secondary bioreactor. The primary bioreactors use anaerobic fermentation to produce acids from a gaseous substrate. At least a portion of the acid product of the one or more primary bioreactors is used as a substrate in one or more secondary bioreactor(s).

Secondary bioreactor—as used herein these terms are intended to encompass any number of further bioreactors that may be connected in series or in parallel with the primary bioreactors. Any one or more of these further bioreactors may also be connected to a further separator.

Fermenting, fermentation process or fermentation reaction—and like terms as used herein, are intended to encompass both the growth phase and product biosynthesis phase of the process. As is described further herein, in some embodiments the bioreactor may comprise a first growth reactor and a second fermentation reactor. As such, the addition of metals or compositions to a fermentation reaction should be understood to include addition to either or both of these reactors.

Processes of producing acids by anaerobic fermentation of gaseous substrates are known in the art.

While the following description focuses on certain embodiments of the invention, it should be appreciated that the invention may be applicable to production of other alcohols and or acids and the use of other substrates as will be known by persons of ordinary skill in the art to which the invention relates upon consideration of the present disclosure. Also, while particular mention is made to fermentation carried out using acetogenic microorganisms, the invention is also applicable to other micro-organisms which may be used in the same or different processes which may be used to produce useful products, including but not limited to other acids and alcohols such as ethanol.

As defined above, in one aspect, the invention relates to processes of producing lipid products from gaseous substrates using a two stage fermentation process. In a first stage a gaseous substrate comprising CO and optionally $H_2$, or $CO_2$ and $H_2$, is anaerobically fermented to produce at least one acid. In the second stage of the process, the at least one acid from the first stage is fed to a second bioreactor containing a culture of at least one microalgae. The at least one acid is aerobically converted to produce one or more lipid products.

The process of one aspect of the invention comprises, culturing, in a primary bioreactor containing a liquid nutrient medium, at least one strain of anaerobic, acetogenic bacteria that are capable of producing acetate from a gaseous substrate containing CO, $CO_2$ or $H_2$, or mixtures thereof, and supplying said gaseous substrate to the bioreactor. The fermentation process produces acetate. The acetate produced in the primary bioreactor is fed to a secondary bioreactor containing a culture of at least one microalgae, capable of producing lipids from an acetate containing substrate.

The at least strain of anaerobic acetogenic bacteria capable of producing acetate from a gaseous substrate containing CO, $CO_2$ or $H_2$, or mixtures thereof are from the group consisting of *Acetobacterium, Moorella, Clostridium, Pyrococcus, Eubacterium, Desulfobacterium, Cabroxydothermus, Acetogenium, Acetoanaerobium, Butyribacetrium, Peptostreptococcus, Ruminococcus, Oxobacter* and *Methanosarcina*.

Fermentation Utilising a Gaseous Substrate

The invention has particular applicability to supporting the production of acetate and ethanol from gaseous substrates comprising CO and optionally $H_2$ containing industrial flue gases. One such type of gas stream is tailgas from steel production plants, which typically contains 20-70% CO. Such gas streams may further comprise $CO_2$. Similar streams are produced from processing of any carbon based feedstock, such as petroleum, coal, and biomass. The invention may also be applicable to reactions which produce alternative acids.

Processes for the production of acetate and other alcohols from gaseous substrates are known. Exemplary processes include those described for example in WO2007/117157, WO2008/115080, U.S. Pat. Nos. 6,340,581, 6,136,577, 5,593,886, 5,807,722 and 5,821,111, each of which is incorporated herein by reference.

A number of anaerobic bacteria are known to be capable of carrying out the fermentation of CO to ethanol and acetic acid and are suitable for use in the process of the present invention. Acetogens have the ability to convert gaseous substrates such as $H_2$, $CO_2$ and CO into products including acetic acid, ethanol and other fermentation products by the Wood-Ljungdahl pathway. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, and *Clostridium autoethanogenum* (Aribini et al, *Archives of Microbiology* 161: pp 345-351). Other suitable bacteria include those of the genus *Moorella*, including *Moorella* sp HUC22-1, (Sakai et al, *Biotechnology Letters* 29: pp 1607-1612), and those of the genus *Carboxydothermus* (Svetlichny, V. A., Sokolova, T. G. et al (1991), *Systematic and Applied Microbiology* 14: 254-260). The disclosures of each of these publications are fully incorporated herein by reference. In addition, other acetogenic anaerobic bacteria may be selected for use in the process of the invention by a person of skill in the art. It will also be appreciated that a mixed culture of two or more bacteria may be used in the process of the present invention.

One preferred micro-organism suitable for use in the present invention is *Clostridium autoethanogenum* that is available commercially from the Deutsche Sammlung von Mikroorganismen and Zellkulturen GmbH (DSMZ) and having the identifying characteristics of DSMZ deposit number DSMZ 10061.

The invention has further applicability to supporting the production of acetate from gaseous substrates comprising $CO_2$ and $H_2$. *Acetobacterium woodii* has been shown to produce acetate by fermentation of gaseous substrates comprising $CO_2$ and $H_2$. Buschhorn et al. demonstrated the ability of *A woodii* to produce ethanol in a glucose fermentation with a phosphate limitation. One exemplary microorganism suitable for use in the present invention is *Acetobacterium woodii* having the identifying characteristics of the strain deposited at the German Resource Centre for Biological Material (DSMZ) under the identifying deposit number DSM 1030.

Other suitable bacteria include those of the genus *Moorella*, including *Moorella sp* HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Morella thermoacetica, Moorella thermoautotrophica, Ruminococcus productus, Acetobacterium woodii, Eubacterium limosum, Butyribacterium methylotrophicum, Oxobacter pfennigii, Methanosarcina barkeri, Methanosarcina acetivorans, Desulfotomaculum kuznetsovii* (Simpa et. al. Critical Reviews in Biotechnology, 2006 Vol. 26. Pp41-65). In addition, it should be understood that other acetogenic anaerobic bacteria may be applicable to the present invention as would be understood by a person of skill in the art. It will also be appreciated that the invention may be applied to a mixed culture of two or more bacteria.

Culturing of the bacteria used in a method of the invention may be conducted using any number of processes known in the art for culturing and fermenting substrates using anaerobic bacteria. Exemplary techniques are provided in the "Examples" section below. In certain embodiments a culture of a bacterium of the invention is maintained in an aqueous culture medium. Preferably the aqueous culture medium is a minimal anaerobic microbial growth medium. Suitable media are known in the art and described for example in U.S. Pat. Nos. 5,173,429 and 5,593,886 and WO 02/08438, and in Klasson et al [(1992). Bioconversion of Synthesis Gas into Liquid or Gaseous Fuels. Enz. Microb. Technol. 14:602-608.], Najafpour and Younesi [(2006). Ethanol and acetate synthesis from waste gas using batch culture of *Clostridium ljungdahlii*. Enzyme and Microbial Technology, Volume 38, Issues 1-2, p. 223-228] and Lewis et al [(2002). Making the connection-conversion of biomass-generated producer gas to ethanol. Abst. Bioenergy, p. 2091-2094]. In particular embodiments of the invention, the minimal anaerobic microbial growth medium is as described hereinafter in the Examples section. By way of further example, those processes generally described in the following disclosures using gaseous substrates for fermentation may be utilised: WO98/00558, M. Demler and D. Weuster-Botz (2010). Reaction Engineering Analysis of Hydrogenotrophic Production of Acetic Acid by *Acetobacterium woodii*. Biotechnology and Bioengineering 2010; D. R. Martin, A. Misra and H. L. Drake (1985). Dissimilation of Carbon Monoxide to Acetic Acid by Glucose-Limited Cultures of *Clostridium thermoaceticum*. Applied and Environmental Microbiology, Vol 49, No. 6, pages 1412-1417. Typically, fermentation is carried out in any suitable bioreactor, such as a continuous stirred tank reactor (CTSR), a bubble column reactor (BCR) or a trickle bed reactor (TBR). Also, in some embodiments of the invention, the bioreactor may comprise a first, growth reactor in which the micro-organisms are cultured, and a second, fermentation reactor, to which fermentation broth from the growth reactor is fed and in which most of the fermentation product (ethanol and acetate) is produced.

Feedstock

Preferably the carbon source for the fermentation can be a gaseous substrate comprising carbon monoxide optionally in combination with hydrogen. Similarly, the gaseous substrate may be a CO and optionally $H_2$ containing waste gas obtained as a by-product of an industrial process, or from some other source.

As described above, the carbon source for the fermentation reaction is a gaseous substrate containing CO. The gaseous substrate may further comprise $CO_2$ and $H_2$. The gaseous substrate may be a CO or $CO_2$-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

In addition, it is often desirable to increase the CO or $CO_2$ concentration of a substrate stream (or partial pressure in a gaseous substrate) and thus increase the efficiency of fermentation reactions where CO or $CO_2$ is a substrate. Increasing CO or $CO_2$ partial pressure in a gaseous substrate increases mass transfer into a fermentation media. The composition of gas streams used to feed a fermentation reaction can have a significant impact on the efficiency and/or costs of that reaction. For example, O2 may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

Hydrogen rich gas streams are produced by a variety of processes including steam reformation of hydrocarbons, and in particular steam reformation of natural gas. The partial oxidation of coal or hydrocarbons is also a source of hydrogen rich gas. Other sources of hydrogen rich gas include the electrolysis of water, by-products from electrolytic cells used to produce chlorine and from various refinery and chemical streams.

The gaseous substrate may further, or instead, comprise $CO_2$. Gas streams with high $CO_2$ content are derived from a variety of industrial processes and includes exhaust gasses from combustion of hydrocarbons, such as natural gas or oil. These processes include cement and lime production, and iron and steel production.

Blending of Streams

As noted previously, it may be desirable to blend an industrial waste stream with one or more further streams in order to improve efficiency, acid and/or alcohol production and/or overall carbon capture of the fermentation reaction.

Accordingly, where industrial streams have a high CO or $CO_2$ content, but include minimal or no $H_2$, it may be desirable to blend one or more streams comprising $H_2$ with the waste stream comprising CO or $CO_2$, prior to providing the blended substrate stream to the fermenter. The overall efficiency, alcohol productivity and/or overall carbon capture of the fermentation will be dependent on the stoichiometry of the CO and $H_2$ or $CO_2$ and $H_2$ in the blended stream. However, in particular embodiments the blended stream may substantially comprise CO and $H_2$ the following molar ratios: at least 1:2 at least 1:4 or at least 1:6 or at least 1:8 or at least 1:10. In particular embodiments the blended stream may comprise CO2 and H2 in the following molar ratios: at least 1:4 or at least 1:6 or at least 1:8 or at least 1:10.

Blending of streams may also have further advantages, particularly in instances where a waste stream comprising CO, $CO_2$ or $H_2$ is intermittent in nature. For example, an intermittent waste stream comprising CO and optionally $H_2$ may be blended with a substantially continuous stream comprising CO and/or $H_2$ and provided to the fermenter. In particular embodiments of the invention, the composition and flow rate of the substantially continuous stream may be varied in accordance with the intermittent stream in order to maintain provision of a substrate stream of substantially continuous composition and flow rate to the fermenter.

Blending of two or more streams to achieve a desirable composition may involve varying flow rates of all streams, or one or more of the streams may be maintained constant while other stream(s) are varied in order to 'trim' or optimise the substrate stream to the desired composition. For streams that are processed continuously, little or no further treatment (such as buffering) may be necessary and the stream can be provided to the fermenter directly. However, it may be necessary to provide buffer storage for streams where one or more is available intermittently, and/or where streams are available continuously, but are used and/or produced at variable rates.

Those skilled in the art will appreciate it will be necessary to monitor the composition and flow rates of the streams prior to blending. Control of the composition of the blended stream can be achieved by varying the proportions of the constituent streams to achieve a target or desirable composition. For example, a base load gas stream may be predominantly CO, and a secondary gas stream comprising a high concentration of $H_2$ may be blended to achieve a specified $H_2$:CO ratio. The composition and flow rate of the blended stream can be monitored by any means known in the art. The flow rate of the blended stream can be controlled independently of the blending operation; however the rates at which the individual constituent streams can be drawn must be controlled within limits. For example, a stream produced intermittently, drawn continuously from buffer storage, must be drawn at a rate such that buffer storage capacity is neither depleted nor filled to capacity.

At the point of blending, the individual constituent gases will enter a mixing chamber, which will typically be a small vessel, or a section of pipe. In such cases, the vessel or pipe may be provided with static mixing devices, such as baffles, arranged to promote turbulence and rapid homogenisation of the individual components.

Buffer storage of the blended stream can also be provided if necessary, in order to maintain provision of a substantially continuous substrate stream to the bioreactor.

A processor adapted to monitor the composition and flow rates of the constituent streams and control the blending of the streams in appropriate proportions, to achieve the required or desirable blend may optionally be incorporated into the system. For example, particular components may be provided in an as required or an as available manner in order to optimise the efficiency of acetate productivity and/or overall carbon capture.

In certain embodiments of the invention, the system is adapted to continuously monitor the flow rates and compositions of at least two streams and combine them to produce a single blended substrate stream of optimal composition, and means for passing the optimised substrate stream to the fermenter.

By way of non limiting example, particular embodiments of the invention involve the utilisation of carbon monoxide gas from a steel production process. Typically, such streams contain little or no $H_2$, therefore it may be desirable to combine the stream comprising CO with a stream comprising $H_2$ in order to achieve a more desirable CO:$H_2$ ratio. $H_2$ is often produced in large quantities at a steel mill in the coke oven. Accordingly, a waste stream from the coke oven comprising $H_2$ can be blended with a steel mill waste stream comprising CO to achieve a desirable composition.

Substrate streams derived from an industrial source are typically variable in composition. Furthermore, substrate streams derived from industrial sources comprising high CO concentrations (such as, for example, at least 40% CO, at least 50% CO or at least 65% CO) often have a low H2 component (such as less than 20% or less than 10% or substantially 0%). As such, it is particularly desirable that micro-organisms are capable of producing products by anaerobic fermentation of substrates comprising a range of CO and $H_2$ concentrations, particularly high CO concentrations and low $H_2$ concentrations. The bacteria of the present invention have a surprisingly high growth rate and acetate production rate while fermenting a substrate comprising CO (and no $H_2$).

It will be appreciated that the processes of the present invention as described herein can be used to reduce the total atmospheric carbon emissions from industrial processes, by capturing CO-containing gases produced as a result of such processes and using them as substrates for the fermentation processes described herein.

Alternatively, in other embodiments of the invention, the CO-containing gaseous substrate may be sourced from the gasification of biomass. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use in the present invention.

It is generally preferred that the CO-containing gaseous substrate contains a major proportion of CO. In particular embodiments, the gaseous substrate comprises at least about 25%, at least about 30%, at least about 40%, at least about 50%, at least about 65%, or at least about 70% to about 95% CO by volume. It is not necessary for the gaseous substrate to contain any hydrogen. The gaseous substrate also optionally contain $CO_2$, such as about 1% to about 30% by volume, such as about 5% to about 10% $CO_2$.

Reaction Stoichiometry

Anaerobic bacteria have been demonstrated to produce ethanol and acetic acid from CO, $CO_2$ and $H_2$ via the Acetyl-CoA biochemical pathway.

The stoichiometry for the formation of acetate from a substrate comprising CO by acetogenic microorganisms is as follows:

$$4CO + 2H_2O \rightarrow CH_3COOH + 2CO_2$$

And in the presence of $H_2$:

$$4CO + 4H_2 \rightarrow 2CH_3COOH$$

Anaerobic bacteria have also been demonstrated to produce acetic acid from $CO_2$ and $H_2$. The stoichiometry for the formation of acetate from a substrate comprising $CO_2$ and $H_2$ by acetogenic bacteria including *Acetobacterium woodii*:

$$4H_2 + 2CO_2 \rightarrow CH_3COOH + 2H_2O$$

It will be appreciated that for growth of the bacteria and CO, or $CO_2$ and $H_2$-to-acetate fermentation to occur, in addition to the CO, $CO_2$ and/or $H_2$-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438 as well as other publications referred to herein before. In one embodiment of the invention the media is as described in the Examples section herein after.

The fermentation should desirably be carried out under appropriate conditions for the CO, or $CO_2$ and $H_2$-to-acetate fermentation to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO or $CO_2$ in the liquid phase does not become limiting, and maximum product concentrations to avoid product inhibition.

In one embodiment, the fermentation is carried out at a temperature of about 34° C. to about 37° C. In a particular embodiment, the fermentation is carried out at a temperature of about 34° C. The inventors note that this temperature range may assist in supporting or increasing the efficiency of fermentation including, for example, maintaining or increasing the growth rate of bacteria, extending the period of growth of bacteria, maintaining or increasing production of metabolites (including acetate), maintaining or increasing CO or $CO_2$ uptake or consumption.

The optimum reaction conditions will depend partly on the particular micro-organism of the invention used. However, in general, it is preferred that the fermentation be performed at pressure higher than ambient pressure. Operating at increased pressures allows a significant increase in the rate of CO and/or $CO_2$ transfer from the gas phase to the liquid phase where it can be taken up by the micro-organism as a carbon source for the production of acetate. This in turn means that the retention time (defined as the liquid volume in the bioreactor divided by the input gas flow rate) can be reduced when bioreactors are maintained at elevated pressure rather than atmospheric pressure.

Also, since a given CO, or $CO_2$ and $H_2$-to-acetate conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment.

Microalgae Utilising Acids as a Substrate for Lipid Production

The invention has particular applicability to supporting the production of lipids from acetate containing substrates. One such type of substrate is acetate derived from the conversion of gaseous substrates comprising CO, or $CO_2$ and $H_2$, or mixtures thereof by anaerobic microbial fermentation.

A number of microalgae are known to be capable of carrying out the fermentation of sugars to lipids, and are suitable for use in the process of the present invention. Examples of such microalgae are those of the genus *Schizochytrium* or *Scenedesmus*.

Microalgae have been shown to produce lipids by heterotrophic fermentation of substrates comprising acetate (Huang, G, Chen, F., Wei, D., Zhang, X., Chen, G. "Biodiesel production by microalgal biotechnology" Applied Energy, Vol 87(1), 2010, 38-46; Ren, H., Liu, B., Ma, C., Zhao, L., Ren, N. "A new lipid-rich microalga *Scenedesmus* sp. strain R-16 isolated using Nile red staining: effects carbon and nitrogen sources and initial pH on the biomass and lipid production. *Biotechnology for Biofuels*, 2013, 6(143)).

Production of lipid(s) by microalgae may be improved by a nitrogen limitation. In particular embodiments, a carbon to nitrogen ratio of 49:1 has a significant impact on lipid production.

The ability of *C. curvatus* to grow on acetate and ethanol, make the product streams of the CO and $H_2$, or $CO_2$ and $H_2$, fermentation process described herein ideal feestocks for the microalgae conversion process. The product stream from the $CO_2/H_2$ fermentation is particularly ideal, as it is rich in acetate. In particular embodiments of the invention, the pH of the product stream from the fermentation can be adjusted to about pH 7.

Suitable microalgae for use in the process of the invention include those of the genus *Chlorella, Chlamamydomonas, Dunaliella, Euglena, Parvum, Tetraselmis, Porphyridium, Spirulina, Synechoccus, Anabaena, Schizochytrium, Botyrococcus, Fucus, Parachlorella, Pseudochlorella, Brateococcus, Prototheca* and *Scenedesmus, Thraustochytrium, Japonochytrium, Aplanochytrium, Elina*, and *Labyrinthula* (or *Labyrinthuloides* or *Labyrinthulomyxa*). In a preferred embodiment, the microalgae is a thraustochytrid of the genus *Thraustochytrium*. The thraustochytrid may be any species of *Thraustochytrium* including, but not limited to, the thraustrochytrids described in Gupta, *Biotechnol Adv*, 30: 1733-1745 (2012) or Gupta, *Biochem Eng*, 78: 11-17 (2013).

In addition, it should be understood that other microalgae may be applicable to the present invention as would be understood by a person of skill in the art. It will also be appreciated that the invention may be applied to a mixed culture of two or more microalgae species.

Culturing of the microalgae used in a method of the invention may be conducted using any number of processes known in the art.

Typically, the conversion process is carried out in any suitable bioreactor, such as a continuous stirred tank reactor (CTSR), a bubble column reactor (BCR) or a trickle bed reactor (TBR). In certain embodiments, the microalgae bioreactor will require an oxygen or air inlet for growth of the microalgae.

In various embodiments, the microalgae contained within the secondary bioreactor are capable of converting acetate to lipids, wherein the lipids accumulate within the membrane fraction of the biomass. Following lipid accumulation, the biomass of the secondary bioreactor can be passed to an extraction system. In certain embodiments, the extraction system is utilised for extraction of accumulated lipids from the membrane fraction of the microalgae biomass. Lipid extraction may be conducted using any number of processes known in the art.

The lipids produced by the process of the invention may be further processed to provide chemicals, fuels or fuel components selected from the group comprising diesel, hydrocarbons, HDRD, FAME and FAEE by means well known in the art. Various derivatives, such as cleaning and personal care products, use components such as surfactants, fatty alcohols, and fatty acids, all of which lipids may be provided as a substitute. Further, various oleochemicals can be produced from lipids.

Media Recycle

The efficiency of the fermentation processes of the various aspects of the invention can be further improved by a further process of recycling a stream exiting the secondary bioreactor to at least one primary reactor. The stream exiting the secondary bioreactor may contain unused metals, salts and other nutrient components. By recycling the exit stream to a primary reactor, the cost of providing a continuous nutrient media to the primary reactor can be reduced. This recycling step has the further benefit of reducing the water requirements of the continuous fermentation process. The stream exiting the bioreactor can be treated before being passed back to a primary reactor.

Furthermore, the recycling step is beneficial because it helps reduce pH control costs in the primary bioreactor. Accumulation of acetate product results in a lowering of the pH in the broth of the primary bioreactor, which is harmful to the culture suspended in the media. In such instances of acetate accumulation, a base, such as $NH_3$ or NaOH, must be added to the media to increase the pH. By passing broth to the secondary bioreactor and then recycling it back to the primary bioreactor, the microalgae of the secondary bioreactor are utilised to consume the acetate and, therefore, increase the pH of the media returned to the primary bioreactor. This reduces the need for the addition of expensive bases to the media of the primary reactor, as acetate is removed from the system via the secondary bioreactor.

In preferred embodiments, the biomass is separated and processed to recover one or more lipid products. The substantially biomass free stream can then be passed to a primary reactor. Alternatively the biomass free stream can be further treated to remove soluble proteins or other unwanted components prior to being passed to the primary reactor. Additional metals and salts can be added to the stream returning to the primary reactor to provide a nutrient stream having a desired composition. The pH of the stream is monitored and adjusted according the fermentation process occurring in the primary reactor.

As in various embodiments, the microalgae require oxygen for growth in the secondary bioreactor, any media recycled back to the primary bioreactor will need to have all oxygen substantially removed, as any oxygen present in the primary bioreactor will be harmful to the anaerobic culture. Therefore, the broth stream exiting the secondary bioreactor may be passed through an oxygen scrubber to remove substantially all of the oxygen prior to being passed to the primary reactor.

The methods and systems of the invention are herein described with reference to the Figures.

FIG. 1 demonstrates a two stage system for the production of lipid(s) from a gaseous stream comprising CO and $H_2$, or $CO_2$ and $H_2$. The system provides a primary bioreactor 101 having a media inlet 102, a gas inlet port 103, a separator means 104, a permeate stream outlet 107, and a bleed stream outlet 108. The primary bioreactor is connected to a secondary bioreactor 201, having a separator 205, a permeate stream outlet 207 and a bleed stream outlet 208.

In use, the primary bioreactor 101 contains fermentation broth comprising a culture of one or more acetogenic bacteria in a liquid nutrient medium. Medium is added to the bioreactor 101 in a continuous or semi-continuous manner throughout the media inlet 102. A gaseous substrate is supplied to the bioreactor 101 via the gas inlet port 103. The separator means is adapted to receive at least a portion of broth from the bioreactor 101 via a first output conduit 104 and pass it through the separator 105 configured to substantially separate the microorganism cells (the retentate) from the rest of the fermentation broth (the permeate). At least a portion of the retentate is returned to the first bioreactor via a first return conduit 106 which ensures that the broth culture density is maintained at an optimal level. The separator 105 is adapted to pass at least a portion of the permeate out of the bioreactor 101 via a permeate delivery conduit 107. The permeate deliver conduit fees the cell free permeate to the secondary bioreactor 201. In certain embodiments of the invention, at least a portion of the cell free permeate is removed for product extraction or be recycled prior to the permeate stream being fed to the secondary bioreactor 201. A broth bleed output 108 is provided to directly feed broth from the primary bioreactor 101 to the secondary bioreactor 202. In certain embodiments the broth bleed and permeate bleed are combined prior to being fed to the secondary bioreactor. It may be desirable to purify the stream prior to passing to the secondary bioreactor to ensure a carbon: nitrogen ratio of at least 10:1, or at least 25:1, or at least 49:1.

The secondary bioreactor 202 contains a culture of one more microalgae in a liquid nutrient medium. The secondary bioreactor receives broth and permeates from the primary bioreactor in a continuous or semi-continuous manner through broth bleed output 108 and permeate delivery conduit 107. The separator means is adapted to receive at least a portion of broth from the bioreactor 201 via a first output conduit 204 and pass it through the separator 205 configured to substantially separate the microorganism cells (the retentate) from the rest of the fermentation broth (the permeate). At least a portion of the retentate is returned to the first bioreactor via a first return conduit 206 which ensures that the broth culture density is maintained at an optimal level. The separator 205 is adapted to pass at least a portion of the permeate out of the bioreactor 201 via a permeate removal conduit 207. A broth bleed output 208 is provided to directly remove broth from the secondary bioreactor 201. The broth bleed stream is treated to remove the biomass for lipid extraction using known methods. The substantially biomass free bleed stream and the permeate streams are combined to produce a combines stream. In certain aspects of the invention, the combined stream can be returned to the primary reactor to supplement the liquid nutrient medium being continuously added. In certain embodiments it may be desirable to further process the recycle stream to remove an un-desired by products of the secondary fermentation. In certain embodiments, the pH of the recycle stream may be adjusted, and further vitamins and metals added to supplement the stream.

Figure 2:
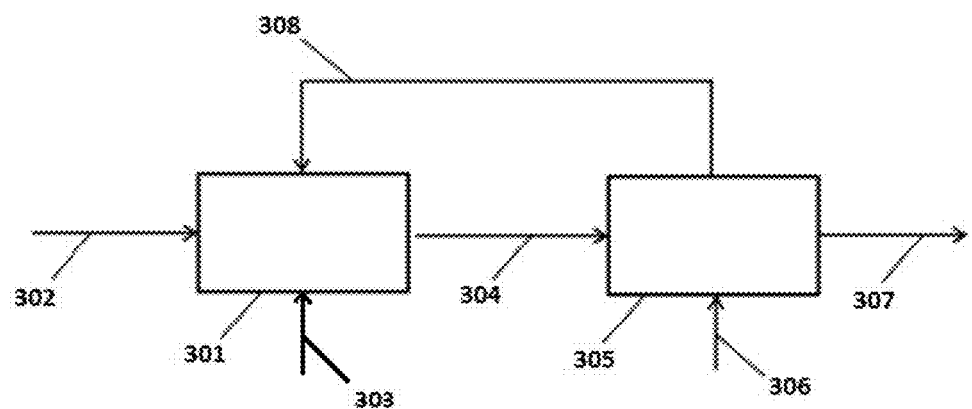
FIG. 2 is a diagram of a two fermenter system for production of lipids from CO and optionally $H_2$, or $CO_2$ and $H_2$, wherein the substantially acetate-free media is recycled from the secondary bioreactor to the primary bioreactor.

FIG. 2 demonstrates a simplified system for the production of lipid(s) from a gaseous stream comprising CO and $H_2$, or $CO_2$ and $H_2$, wherein the substantially acetate-free media is recycled from the secondary bioreactor to the primary bioreactor. The system includes a primary anaerobic bioreactor 301 having a media inlet 302, a gas inlet port 303, an acetate-containing bleed stream 304, a secondary aerobic bioreactor 305, an oxygen source 306, a lipid and biomass-containing product stream 307, and an acetate-depleted recycled media stream.

In use, the primary bioreactor 301 contains fermentation broth comprising a culture of one or more acetogenic bacteria in a liquid nutrient medium. Medium is added to the bioreactor 301 in semi-continuous manner through the media inlet 302. A gaseous substrate comprising either CO and optionally $H_2$, or $CO_2$ and $H_2$, or mixtures thereof, is supplied to the primary bioreactor 301 via a gas inlet port 303, wherein the gas is converted by the bacteria to acetate. The primary bioreactor 301 is maintained at a pH in the range of 6.5-7, with pH partially controlled by the addition of base as necessary. The acetate product leaves the primary bioreactor in an aqueous broth stream 304, which is fed to a secondary aerobic bioreactor 305. In the secondary bioreactor 305, acetate in the aqueous broth is converted to lipids and non-lipid biomass by microalgae. Oxygen is supplied to the aerobic fermentation by an oxygen or air inlet port 306. The lipid-containing microalgae cells are removed from the secondary bioreactor 305 by filtration, resulting in a lipid and biomass containing product stream 307 and a permeate stream 308. Because the aerobic fermentation consumes acetate, the pH of the broth increases as acetate is consumed, and the pH of the permeate stream 308 is consequently nominally higher than the pH of the acetate-containing broth stream 304. The dilution rate of the secondary bioreactor 305 is maintained such that the pH of the permeate stream 308 remains in the range of 7.0-7.5. The acetate-depleted permeate stream 308 is returned to the primary bioreactor 301. In addition to recycling a substantial portion of the water, salts, metals, and other nutrients that make up the media of the primary bioreactor 301, the recycled water stream 308 acts to recycle base used within the system, significantly reducing the cost of fermentation pH control relative to a system in which pH is controlled only by direct addition of base to the bioreactor media.

EXAMPLES

Materials and Methods

Media

| Solution A | | | |
|---|---|---|---|
| $NH_4Ac$ | 3.083 g | KCl | 0.15 g |
| $MgCl_2 \cdot 6H_2O$ | 0.4 g | NaCl (optional) | 0.12 g |
| $CaCl_2 \cdot 2H_2O$ | 0.294 g | Distilled Water | Up to 1 L |

| Solution B | | | |
|---|---|---|---|
| Biotin | 20.0 mg | Calcium D-(*)-pantothenate | 50.0 mg |
| Folic acid | 20.0 mg | Vitamin B12 | 50.0 mg |
| Pyridoxine•HCl | 10.0 mg | p-Aminobenzoic acid | 50.0 mg |
| Thiamine•HCl | 50.0 mg | Thioctic acid | 50.0 mg |
| Riboflavin | 50.0 mg | Distilled water | To 1 Liter |
| Nicotinic acid | 50.0 mg | | |

| Solution C | | | |
|---|---|---|---|
| Component/0.1M solution (aq) | Quantity/ml | Component/0.1M solution (aq) | Quantity/ml |
| $FeCl_3$ | 10 ml | $Na_2MoO_4$ | 0.1 ml |
| $CoCl_2$ | 1 ml | $ZnCl_2$ | 1 ml |
| $NiCl_2$ | 0.1 ml | $Na_2WO_4$ | 0.1 ml |
| $H_3BO_3$ | 1 ml | Distilled water | To 1 Litre |

| Solution D | | | |
|---|---|---|---|
| Component | Conc. (in $H_2O$) | Component | Conc. (in $H_2O$) |
| $FeSO_4$ | 0.1 mol/L | $Na_2MoO_4$ | 0.01 mol/L |
| $CoCl_2$ | 0.05 mol/L | $ZnCl_2$ | 0.01 mol/L |
| $NiCl_2$ | 0.05 mol/L | $H_3BO_3$ | 0.01 mol/L |

| Solution E | | | |
|---|---|---|---|
| Media Component | Quantity | Media Component | Quantity |
| $MgCl_2 \cdot 6H_2O$ | 0.5 g | Solution B | 10 mL |
| NaCl | 0.2 g | Solution C | 10 mL |
| $CaCl_2$ | 0.2 g | Resazurin (2 mg/L stock) | 1 mL |
| $NaH_2PO_4$ | 2.04 g | $FeCl_3$ | 1 ml |
| $NH_4Cl$ | 2.5 g | Cysteine•HCl monohydrate | 0.5 g |
| 85% $H_3PO_4$ | 0.05 ml | Distilled water | To 1 litre |
| KCl | 0.15 g | | |

| Solution F | | | |
|---|---|---|---|
| Component | Quantity | Component | Quantity |
| $FeCl_3$ (0.1M solution) | 30 ml | $Na_2S \cdot 9H_2O$ | 2.8 g |
| $CoCl_2$ (0.1M solution) | 30 ml | Distilled water | To 300 ml |
| $NiCl_2$ (0.1M solution) | 30 ml | | |

The two types of *Clostridium autoethanogenum* used were those deposited at the German Resource Centre for Biological Material (DSMZ) and allocated the accession numbers DSM 19630 and DSM 23693. DSM 23693 was developed from *Clostridium autoethanogenum* strain DSM19630 (DSMZ, Germany) via an iterative selection process.

Bacteria: *Acetobacterium woodii* were obtained from the German Resource Centre for Biological Material (DSMZ). The accession number given to the bacteria is DSM 1030.

Preparation of $Na_2S$—A 500 ml flask was charged with $Na_2S$ (93.7 g, 0.39 mol) and 200 ml $H_2O$. The solution was stirred until the salt had dissolved and sulfur (25 g, 0.1 mol) was added under constant $N_2$ flow. After 2 hours stirring at room temperature, the "$Na_2S_x$" solution (approx 4M with respect to [Na] and approx 5M with respect to sulfur), now a clear reddish brown liquid, was transferred into $N_2$ purged serum bottles, wrapped in aluminum foil.

Preparation of Cr (II) solution—A 1 L three necked flask was fitted with a gas tight inlet and outlet to allow working under inert gas and subsequent transfer of the desired product into a suitable storage flask. The flask was charged with $CrCl_3 \cdot 6H_2O$ (40 g, 0.15 mol), zinc granules [20 mesh] (18.3 g, 0.28 mol), mercury (13.55 g, 1 mL, 0.0676 mol) and 500 ml of distilled water. Following flushing with $N_2$ for one hour, the mixture was warmed to about 80° C. to initiate the reaction. Following two hours of stirring under a constant $N_2$ flow, the mixture was cooled to room temperature and continuously stirred for another 48 hours by which time the reaction mixture had turned to a deep blue solution. The solution was transferred into $N_2$ purged serum bottles and stored in the fridge for future use.

Sampling and Analytical Procedures

Media samples were taken at intervals over a 30 day period

All samples were used to establish the absorbance at 600 nm (spectrophotometer) and the level of substrates and products (GC or HPLC). HPLC was routinely used to quantify the level of acetate.

HPLC: HPLC System Agilent 1100 Series. Mobile Phase: 0.0025N Sulfuric Acid. Flow and pressure: 0.800 mL/min. Column: Alltech IOA; Catalog #9648, 150×6.5 mm, particle size 5 μm. Temperature of column: 60° C. Detector: Refractive Index. Temperature of detector: 45° C.

Method for sample preparation: 400 μL of sample and 50 μL of 0.15M $ZnSO_4$ and 50 μL of 0.15M $Ba(OH)_2$ are loaded into an Eppendorf tube. The tubes are centrifuged for 10 min. at 12,000 rpm, 4° C. 200 μL of the supernatant are transferred into an HPLC vial, and 5 μL are injected into the HPLC instrument.

Headspace Analysis: Measurements were carried out on a Varian CP-4900 micro GC with two installed channels. Channel 1 was a 10 m Mol-sieve column running at 70° C., 200 kPa argon and a backflush time of 4.2 s, while channel 2 was a 10 m PPQ column running at 90° C., 150 kPa helium and no backflush. The injector temperature for both channels was 70° C. Runtimes were set to 120 s, but all peaks of interest would usually elute before 100 s. Headspace of fermenter was analysed automatically by Gas-GC (Varian 4900 Micro-GC) at hourly.

Cell Density: Cell density was determined by counting bacterial cells in a defined aliquot of fermentation broth. Alternatively, the absorbance of the samples was measured at 600 nm (spectrophotometer) and the dry mass determined via calculation according to published procedures.

Example 1: Fermentation of CO in Bioreactor to Produce Acetate

A glycerol stock of a *Clostridium autoethanogenum* was revived in serum bottles. The glycerol stock stored at 80° C. was slowly thawed and transferred into the serum bottle using a syringe. This process was carried out inside an anaerobic chamber. The inoculated serum bottle was subsequently removed from the anaerobic chamber and pressurized to a total of 45 psi using a CO-containing gas mixture (40% CO, 3% H2, 21% CO2, 36% N2). The bottle was then placed horizontally on a shaker inside an incubator at a temperature of 37 C. After two days of incubation and after verifying that the culture grew, the bottle was used to inoculate another set of eight gas containing serum bottles with 5~mL of this culture. These serum bottles were incubated for another day as described above and then used to inoculate 5 L of liquid medium that was prepared in a 10 L CSTR. The initial CO containing gas flow was set at 100~mL/min and the stirring rate was set to a low 200 rpm. When the microbes started consuming gas the agitation and gas flows were increased to 400 rpm and 550 mL/min. After two days of growth in batch mode, the fermenter was turned continuous with a dilution rate of 0.25 l/day. The dilution rate was increased by 0.25 l/day to a value of 1 l/day every 24~h.

Figure 3:
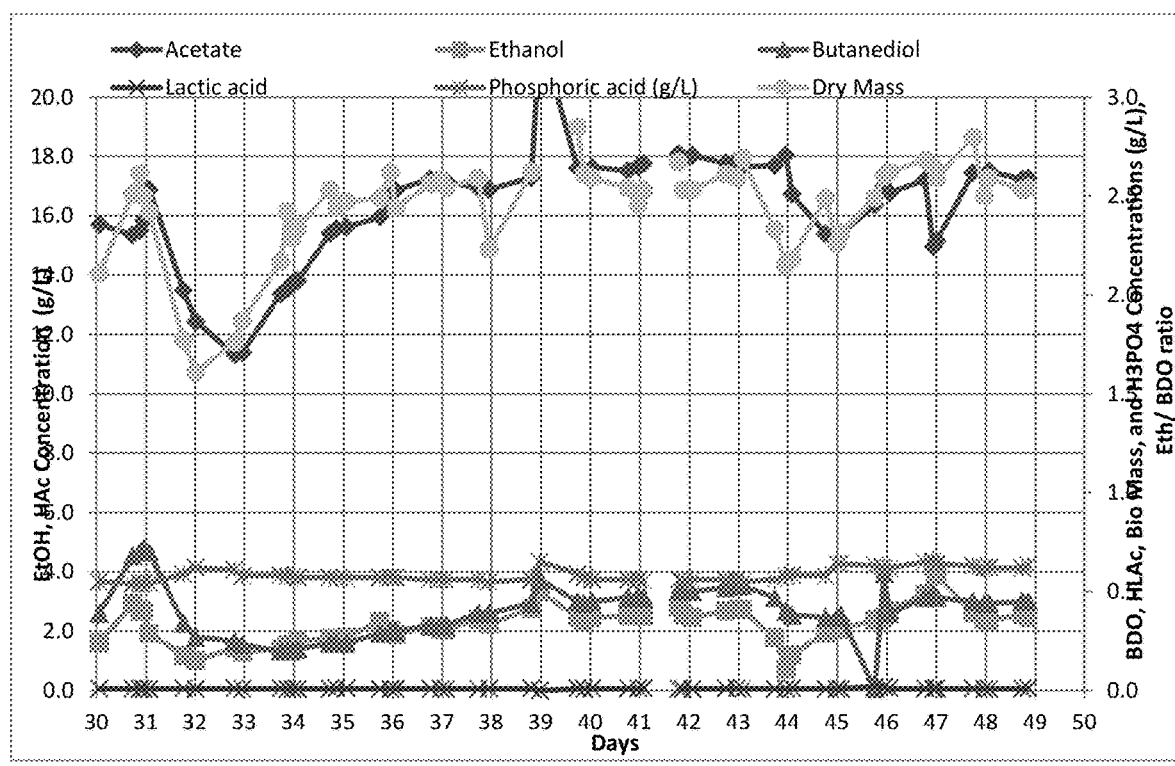
FIG. 3 is a graph showing the acetate concentration in a fermentation utilizing CO accordance with one embodiment of the present invention.

Metabolite and microbial growth can be seen in FIG. 3. Acetate concentration in the reactor carried from between around 10 g/L to over 20 g/L. The dilution rate was 1.0. Productivity rates for acetate were between 10 g/L/day and over 20 g/L/day. The ratio of acetate to ethanol varied between around 5:1 to around 18:1.

Example 2: Fermentation of $CO_2$ and $H_2$ in Bioreactor to Produce Acetate

Media at pH 6.5 was prepared as using the protocol defined by Balch et al (See, e.g., Balch et al, (1977) International Journal of Systemic Bacteriology., 27:355-361). A three-litre reactor was filled with 1500 ml of the media. Oxygen was removed from the media by continuously sparging with $N_2$. The gas was switched from $N_2$ to a mixture of 60% $H_2$, 20% $CO_2$, and 20% $N_2$ 30 minutes before inoculation. The inoculum (150 ml) came from a continuous *Acetobacterium woodii* culture fed with the same gas mixture. The bioreactor was maintained at 30° C. and stirred at 200 rpm at the time of inoculation. During the following batch growth phase, agitation was increased incrementally to 600 rpm. The gas flow was increased incrementally by 50 ml/min according to the dropping $H_2/CO_2$ in the headspace as a result of the increasing biomass. To compensate for the acetic acid produced, the pH was automatically controlled to 7 using 5 M NaOH. Throughout the fermentation, a 0.5M solution of Na2S was pumped into the fermenter at a rate of 0.2 ml/hour. The culture was made continuous after 1 day. To reach high biomass along with high gas consumption, it is necessary to keep the acetate concentration in the fermenter at levels below 20 g/L. This was realized by running the fermenter at a relatively high dilution rate (D~1.7/day) while retaining the microbes in the fermenter with a polysulfone membrane filtration system with 0.1 μm pore size (GE healthcare hallow fibre membrane). The medium for the continuous culture was solution A excluding the composite trace metal solution, which was fed separately at a rate of 1.5 ml/hour using an automated syringe pump. The medium was degassed at least 1 day before and continuously degassing throughout fermentation process.

Results

Over a thirty day period acetate is produced at a concentration of 12.5 g/L. The productivity rate of acetate averaged at 21.8 g/L per day.

The maximum concentration of acetic acid in a continuous culture was 17.76 g/L (296 mM)

Example 3 Microalgae Acetate Utilisation

It has recently been demonstrated that the microalgae may utilise acetate as a carbon source for production of lipids. Ren et al. have shown that *Scenedesmus* sp. cultured in a liquid medium comprising acetate as a carbon source produced a total lipid content 43.4% and a maximum biomass concentration of 1.86 g $L^{-1}$ (Ren, H., Liu, B., Ma, C., Zhao, L., Ren, N. "A new lipid-rich microalga *Scenedesmus* sp. strain R-16 isolated using Nile red staining: effects carbon and nitrogen sources and initial pH on the biomass and lipid production. *Biotechnology for Biofuels*, 2013, 6(143)).

In the present system, acetate derived from anaerobic fermentation of a gaseous substrate is fed to a CSTR comprising microalgae, such as *Scenedesmus* sp. The microalgae is cultured in media at 25° C. and a pH of 7. Agitation is set at 150 rpm. A nitrogen source, such as sodium nitrate, should also be present in the media at a range between 0.1-1.0 g/L, depending on the acetate concentration. Once all acetate in the media is converted to biomass, lipids are extracted from the biomass using known extraction methods.

The reference to any prior art in this specification is not, and should not be taken as, an acknowledgement or any form of suggestion that that prior art forms part of the common general knowledge in the field of endeavour in any country.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

The invention claimed is:

1. A method for producing at least one lipid product from a gaseous substrate, the method comprising:
   i. receiving a gaseous substrate comprising $CO_2$ and $H_2$ in a first bioreactor containing a culture of at least one microorganism in a liquid nutrient medium, and fermenting the gaseous substrate under anaerobic conditions to produce acetate;
   ii. passing at least a portion of the acetate to a second bioreactor containing a culture of at least one microalgae in a liquid nutrient medium, and fermenting the acetate under aerobic conditions to produce at least one lipid product, wherein the microalgae is selected from the group consisting of *Thraustochytrium, Japonochytrium, Aplanochytrium, Elina*, and *Labyrinthula;*
   iii obtaining a fermentation broth from the second bioreactor; and
   iv. passing at least a portion of the fermentation broth from the second bioreactor to a separator to produce a product stream comprising at least one lipid and biomass and an acetate depleted permeate stream;
   v. passing the permeate stream to an oxygen removal unit to remove oxygen and then recycling at least a portion of the resulting oxygen depleted stream to the first bioreactor.

2. The method of claim 1, wherein the production rate of acetate in the first bioreactor is at least 10 g/L/day.

3. The method of claim 1, wherein the at least one microorganism in the first bioreactor is selected from the group consisting of *Acetobacterium, Moorella, Clostridium, Pyrococcus, Eubacterium, Desulfobacterium, Carboxydothermus Acetogenium, Acetoanaerobium, Butyribacterium, Peptostreptococcus, Ruminococcus, Oxobacter*, and *Methanosarcina*.

4. The method of claim 1, wherein the at least one microalgae in the second bioreactor is *Thraustochytrium*.

5. The method of claim 1, further comprising converting the at least one lipid product produced in stage (ii) to a product selected from a hydrogenation-derived renewable diesel (HDRD), fatty acid methyl esters (FAME), fatty acid ethyl esters (FAEE), or biodiesel.

6. The method of claim 1, wherein lipid production is increased in the second bioreactor by limiting at least one nutrient in the liquid nutrient medium.

7. The method of claim 6, wherein the limited nutrient is nitrogen.

8. The method of claim 1, wherein the lipid product is a polyunsaturated fatty acid.

9. The method of claim 8, wherein the polyunsaturated fatty acid is an omega-3 fatty acid.

10. The method of claim 9, wherein the omega-3 fatty acid is one or more of alpha-linolenic acid (ALA), eicosapentaenoic acid (EPA), and docosahexaenoic acid (DHA).

11. The method of claim 1, wherein the at least one microorganism in the first bioreactor is an acetogenic bacterium.

12. The method of claim 1, wherein the microalgae is selected from the group consisting of *Japonochytrium, Aplanochytrium, Elina*, and *Labyrinthula*.

13. The method of claim 1, wherein the liquid nutrient medium of the second bioreactor comprises nitrogen.

14. The method of claim 13, wherein the liquid nutrient medium of the second bioreactor comprises an acetic acid to nitrogen ratio of at least 10:1.

15. The method of claim 13, wherein the liquid nutrient medium of the second bioreactor comprises a carbon to nitrogen ratio of 49:1 or greater.

16. A method for producing at least one lipid product from a gaseous substrate, the method comprising:
   i. receiving a gaseous substrate comprising CO in a first bioreactor containing a culture of at least one microorganism in a liquid nutrient medium, and fermenting the gaseous substrate under anaerobic conditions to produce acetate;
   ii. passing at least a portion of the acetate to a second bioreactor containing a culture of at least one microalgae in a liquid nutrient medium, and fermenting the acetate under aerobic conditions to produce at least one lipid product, wherein the microalgae is selected from the group consisting of *Thraustochytrium, Japonochytrium, Aplanochytrium, Elina*, and *Labyrinthula;*
   iii obtaining a fermentation broth from the second bioreactor;
   iv. passing at least a portion of the fermentation broth from the second bioreactor to a separator to produce a product stream comprising at least one lipid and biomass and an acetate depleted permeate stream;
   v. passing the permeate stream to an oxygen removal unit to remove oxygen and then recycling at least a portion of the resulting oxygen depleted stream to the first bioreactor.

17. The method of claim 16, wherein the at least one microorganism in the first bioreactor is selected from the group consisting of *Acetobacterium, Moorella, Clostridium, Pyrococcus, Eubacterium, Desulfobacterium, Carboxydothermus Acetogenium, Acetoanaerobium, Butyribacterium, Peptostreptococcus, Ruminococcus, Oxobacter*, and *Methanosarcina*.

18. The method of claim 16, wherein the at least one microalgae in the second bioreactor is *Thraustochytrium*.

* * * * *